US009290469B2

(12) United States Patent
Newman et al.

(10) Patent No.: US 9,290,469 B2
(45) Date of Patent: Mar. 22, 2016

(54) PRODUCTION OF OXIDIZED OLEFINS (75) Inventors: Kent Newman, Scott Depot, WV (US);
Bernie Osborne, Hurricane, WV (US);
John Szul, Hurricane, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/125,863

(22) PCT Filed: Jun. 22, 2012

(86) PCT No.: PCT/US2012/043670
§ 371 (c)(1),
(2), (4) Date: Dec. 12, 2013

(87) PCT Pub. No.: WO2013/012518
PCT Pub. Date: Jan. 24, 2013

(65) Prior Publication Data
US 2014/0114083 A1    Apr. 24, 2014

Related U.S. Application Data (60) Provisional application No. 61/500,428, filed on Jun. 23, 2011.

(51) Int. Cl.
*B01J 8/00*    (2006.01)
*B01J 8/02*    (2006.01)
(Continued)

(52) U.S. Cl.
CPC ............... *C07D 301/06* (2013.01); *B01J 8/067* (2013.01); *B01J 19/0013* (2013.01)

(58) Field of Classification Search
CPC .................. B01J 8/00; B01J 8/02; B01J 8/06;
B01J 8/067; B01J 19/00; B01J 19/0006;
B01J 19/0013; B01J 19/24; B01J 19/2415;
B01J 19/2425; C07D 301/00; C07D 301/02;
C07D 301/03; C07D 301/04; C07D 301/06;
C07D 301/10
USPC .......... 422/129, 600, 650–652; 549/200, 512, 549/513, 518, 523, 524, 532, 533
See application file for complete search history.

(56) References Cited

U.S. PATENT DOCUMENTS 2,196,229 A    4/1940    Prickett
2,371,381 A    3/1945    Campbell et al.
(Continued)

FOREIGN PATENT DOCUMENTS

WO    WO 2007/006398 A1 *    1/2007

OTHER PUBLICATIONS

International Search Report and Written Opinion from related PCT Application PCT/US2012/043670, filed Jun. 22, 2012, 16 pgs.

*Primary Examiner* — Natasha Young
(74) *Attorney, Agent, or Firm* — Brooks, Cameron & Huebsch, PLLC (57) ABSTRACT

A system and method for the production of oxidized olefins. The system includes two or more reactors having a number of reaction tubes. A catalyst for catalytic oxidation of olefins is on a first side of the number of reaction tubes. A common supply line supplies a mixture comprising olefins and oxygen to the catalyst. Product outlet streams from each reactor are joined to a single product stream. Coolant fluid passing through the reactors flows into a single coolant drum. The single coolant drum supplies the coolant fluid at a common temperature to a number of coolant fluid inlet streams of each reactor.

14 Claims, 7 Drawing Sheets

(51) Int. Cl.
*B01J 8/06* (2006.01)
*B01J 19/00* (2006.01)
*B01J 19/24* (2006.01)
*C07D 301/06* (2006.01)
*C07D 301/00* (2006.01)
*C07D 301/02* (2006.01)
*C07D 301/03* (2006.01)
*C07D 301/04* (2006.01)
*C07D 301/10* (2006.01)

(56) References Cited

U.S. PATENT DOCUMENTS

| | | |
|---|---|---|
| 2,788,264 A | 4/1957 | Bremer et al. |
| 3,282,652 A | 11/1966 | Barretta |
| 3,290,894 A | 12/1966 | Tsao |
| 5,849,937 A | 12/1998 | Jubin, Jr. et al. |
| 2006/0002831 A1* | 1/2006 | Leffer .......................... 422/188 |
| 2008/0071109 A1 | 3/2008 | Yada et al. |
| 2010/0185001 A1* | 7/2010 | Van Maaren et al. ......... 549/523 |

* cited by examiner

PRODUCTION OF OXIDIZED OLEFINS

CROSS-REFERENCE TO RELATED APPLICATIONS

This application is a National Stage Application under 35 U.S.C. §371 of International Application Number. PCT/US2012/043670, filed Jun. 23, 2012 and published as WO 2013/012518 on Jan. 24, 2013, which claims the benefit to U.S. Provisional Application 61/500,428, filed Jun. 23, 1211, the contents of which are incorporated herein by reference in its entirety.

FIELD OF DISCLOSURE

The present disclosure relates to a system and method for an oxidation of hydrocarbon, and in particular a system and method for the oxidation of an olefin.

BACKGROUND

An olefin (e.g., alkene) is an unsaturated hydrocarbon containing one or more pairs of carbon atoms linked by a double bond. Olefins are classified in either or both of the following ways: (1) as cyclic or acyclic (aliphatic) olefins, in that the double bond is located between carbon atoms forming part of a cyclic (closed-ring) or of an open-chain grouping, respectively, and (2) as monoolefins, diolefins, triolefins, etc., in that the number of double bonds per molecule is, respectively, one, two, three, or some other number. Olefins containing two to four carbon atoms per molecule are gaseous at ordinary temperatures and pressures; those containing five or more carbon atoms are usually liquid at ordinary temperatures and pressures. Oxidation of an olefin occurs when the functional group (e.g., double carbon-carbon bond) is broken (e.g., cracked) to allow an oxygen molecule to attach to the hydrocarbon.

Oxidized olefins are used in many chemical processes. For example, ethylene oxide is an important raw material in many large scale chemical productions, such as ethylene glycols, ethylene glycol ethers, and ethoxylates. Ethylene glycol and the other derivatives produced from the oxidized olefin ethylene oxide can be found in antifreeze, in the production of polyester, and polyethylene terephthalate, liquid coolants and solvents, perfumes, cosmetics, pharmaceuticals, lubricants, paint thinners, and plasticizers. Ethylene glycol ethers are part of brake fluids, detergents, solvents, lacquers, and paints. Ethoxylates are reaction products of ethylene oxide with higher alcohols, acids or amines. They are used in the manufacture of detergents, surfactants, emulsifiers, and dispersants.

The production of oxidized olefins via direct oxidation is generally known. The oxidation involves catalytic oxidation of an olefin with oxygen over a catalyst to yield an oxidized olefin. Generally, the process can be divided into two processes depending on the source of the oxidizing agent—the air-based process and the oxygen based process. In the first, air or air enriched with oxygen is fed directly to the system. In the second, a high purity oxygen stream (e.g., greater than 98 mol %) from an air separation unit is employed as the source of the oxidizing agent.

Normally the reaction vessel and the oxidized olefin product are cooled to prevent further reaction of the oxidized olefin (e.g., isomerisation). Failure to cool the oxidized olefin product could result in further reactions that could render undesired byproducts. Further, reaction vessel temperature control is a concern, as the oxidation of olefins is a highly exothermic reaction and without proper temperature control mechanisms could result in a "runaway reaction." Typically the reaction vessel temperature can be controlled via a coolant circulating through the reaction vessel, controlling the promoter concentration, or both.

SUMMARY

Embodiments of the present disclosure include a system for the production of oxidized olefins. For the various embodiments, the system includes two or more reactors including a number of reaction tubes each having a first surface defining a first side and a second surface opposite the first surface that defines a second side of each the tubes. For the various embodiments, a catalyst for catalytic oxidation of olefins can be located on the first side of the number of reaction tubes. A common supply line supplies inlets to each of the two or more reactors that provide a mixture comprising olefins and oxygen to the catalyst.

Product outlet streams of the two or more reactors receive the oxidized olefin product and are joined to a single product stream. Coolant fluid passes through the two or more reactors to remove heat from the number of reaction tubes and flows into a single coolant drum connected to the two or more reactors. The single coolant drum receives the coolant fluid from a number of coolant fluid outlet streams of each of the two or more reactors. The single coolant drum supplies the coolant fluid at a common temperature to a number of coolant fluid inlet streams of each of the two or more reactors so the coolant fluid passes through each of the two or more reactors.

Embodiments of the present disclosure also provide for the catalyst on the first side of the number of reaction tubes of each of the two or more reactors to deactivate at a substantially equivalent rate.

Embodiments of the present disclosure also include a method for producing oxidized olefins. For the various embodiments, the method includes supplying a mixture comprising olefins and oxygen to two or more reactors from a common supply line. The mixture is reacted in each of the two or more reactors to produce a product stream of the oxidized olefins for each reactor. The product stream from each of the two or more reactors is joined into a single common product stream comprising the oxidized olefins. Coolant fluid is supplied from each reactor to a single coolant drum by a number of coolant fluid outlet streams of each reactor. The single coolant drum supplies the coolant fluid at a common temperature to each of the two or more reactors to remove heat produced in the two or more reactors during the reaction of the mixture.

Embodiments of the present disclosure also provide maintaining a promoter concentration feed of each of the two or more reactors within a tolerance level. In various embodiments, coolant fluid outlet and inlet piping is designed for providing substantially equivalent cooling of each of the two or more reactors.

DEFINITIONS

As used herein, "olefin" (e.g., alkene) is a hydrocarbon with a carbon-carbon double bond. More than one molecule of the olefin is referred to herein as "olefins." Olefins can include more than one molecule of each olefin in a mixture of olefins.

As used herein, "ethylene oxide" (e.g., oxirane) has the chemical formula $C_2H_4O$ at standard temperature and pressure of 0° C. and absolute pressure of 100 kPa (IUPAC).

As used herein, an "indirect heat exchanger" is defined as a device in which heat is transferred between one medium and another, where the media are separated by a solid wall so that they do not mix. Such indirect heat exchangers can include, but are not limited to, shell and tube heat exchangers, plate heat exchangers (e.g., plate and frame), cross heat exchangers, among others.

As used herein, "group" is defined as is known in the art according to the standard periodic table, version dated Feb. 19, 2010, by International Union of Pure and Applied Chemistry (IUPAC).

As used herein, "deactivation" is the loss of catalytic activity and/or selectivity over time.

As used herein, "inert" is defined as a substituent that is non-reactive in the system and method of the present disclosure.

As used herein, "° C." is defined as degrees Celsius.

As used herein, "Pa" is defined as a Pascal. A Pascal is equivalent to 1 N/m².

As used herein, "ambient temperature" is defined as the temperature of the environment in that the process of the present disclosure is operated. Heat exchange fluid at ambient temperature according to the present disclosure is used without actively extracting heat therefrom.

As used herein, "a single coolant drum" is defined as only one coolant drum of typical construction as is known in the art to separate the vapor phase of the coolant fluid from the liquid phase of the coolant fluid (e.g., size of the single coolant drum is determined by total heat load).

As used herein, "a," "an," "the," "a number of," "at least one," and "one or more" are used interchangeably. The terms "comprises" and variations thereof do not have a limiting meaning where these terms appear in the description and claims. Thus, for example, a reactor having a number of reaction tubes can be interpreted to mean that the reactor includes "one or more" reaction tubes.

As used herein, the term "and/or" means one, more than one, or all of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION

Embodiments of the present disclosure include a system and method for the production of oxidized olefins. For the various embodiments, the system and method include two or more reactors having a number of reaction tubes each having a first surface defining a first side and a second surface opposite the first surface that defines a second side of each the tubes. For the various embodiments, a catalyst for catalytic oxidation of olefins can be located on the first side of the number of reaction tubes. A common supply line supplies to inlets of each reactor a mixture comprising olefins and oxygen to the catalyst. Product outlet streams of each reactor receive the oxidized olefin product and are joined into a single product stream. Coolant fluid passes through the reactors via a number of coolant fluid inlet streams to each reactor to remove heat from the number of reaction tubes. The coolant fluid flows from a number of coolant fluid outlet streams of each of the reactors into a single coolant drum connected to the two or more reactors. So, a single coolant drum receives the coolant fluid from a number of coolant fluid outlet streams of each of the reactors. The single coolant drum supplies the coolant fluid at a common temperature to the number of coolant fluid inlet streams of each reactor.

In simplifying the process for producing oxidized olefins, embodiments of the present disclosure allow for fewer mechanical components to be used in producing the oxidized olefin product. Examples of such mechanical components include those used to move raw material, coolant fluid, and oxidized olefin product, such as pumps and other components that have parts that either rotate and/or move relative to each other. As the reaction for the oxidation of olefins is exothermic, there can be build-up of heat in the various mechanical components, from either incidental or intended reactions. By reducing the need for such mechanical components there is a corresponding reduction in the opportunity for problems to arise in the system and method for producing the oxidized olefin product according to the present disclosure.

In addition, the embodiments of the present disclosure allow for fewer vessels and piping to be used in the system for production of the oxidized olefin product. Examples of such vessels include coolant drums, for the reactor coolant fluid and the aftercooler coolant makeup fluid, as well as heat exchangers to cool the oxidized olefin product and preheat the supply mixture line. Maintaining temperature control within the system for the production of oxidized olefins increases oxidized olefin product yield as well as reduces the opportunity for "run-away reaction" incidents. Additional embodiments of the present disclosure allow for the catalyst of each of the multiple reaction vessels to deactivate at the same rate. Allowing the catalyst of each of the multiple reactors to deactivate at the same rate increases predictability of shutdowns for catalyst replacement of the two or more reactors, further increasing overall system efficiency by reducing the downtime required for replacing the catalyst. In addition, replacing the catalyst in the two or more reactors at the same time can reduce the amount of piping, valves, and flanges in the system, which accordingly reduces the opportunity for leaks and/or emissions.

In the following detailed description of the present disclosure, reference is made to an accompanying drawing that forms a part hereof, and in that is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, chemical and/or structural changes may be made without departing from the scope of the present disclosure.

The figures herein follow a numbering convention in that the first digit corresponds to the drawings figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the present disclosure. In addition, as will be appreciated the proportion and the relative scale of the elements provided in the figures are intended to illustrate the embodiments of the present invention, and should not be taken in a limiting sense.

Figure 1:
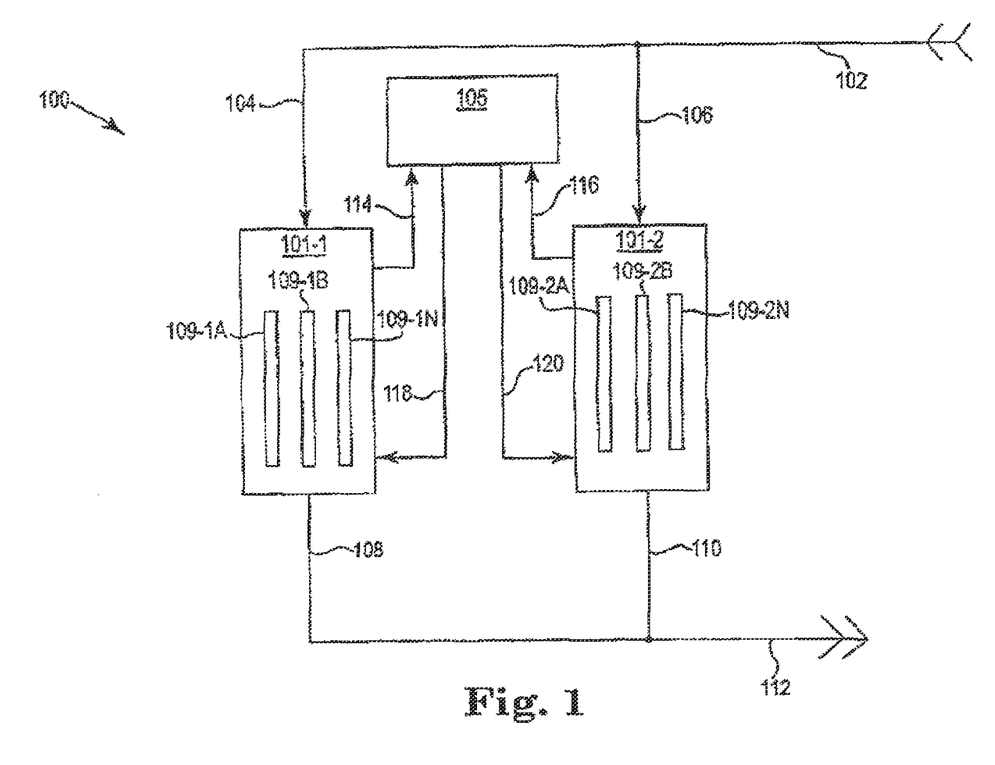
FIG. 1 provides a schematic of a process for producing an oxidized olefin product according to an embodiment of the present disclosure.

Referring to FIG. 1, there is illustrated a schematic of a system 100 for the production of an oxidized olefin product. For the system 100, two or more reactors 101-1, 101-2 include a number of reaction tubes 109-1A, 109-1B, 109-1N and 109-2A, 109-2B, 109-2N, where N represent N number of reaction tubes. The number of reaction tubes 109-1A, 109-1B, 109-1N and 109-2A, 109-2B, 109-2N each have a first surface defining a first side and a second surface opposite the first surface that defines a second side of each the tubes, where catalyst can be on the first side of the number of reaction tubes 109-1A, 109-1B, 109-1N and 109-2A, 109-2B, 109-2N. Various embodiments are not as limited as having structurally identical reactors for the two or more reactors 101-1, 101-2. Examples of such reactors include, but are not limited to, vertical shell-and-tube, fixed-bed, transport bed, fluidized bed, moving bed, and trickle bed. For example, shell-and-tube side reactors can include reaction tubes each having a first surface defining a first side and a second surface opposite the first surface that defines a second side of each the tubes. For the various embodiments, the first side of the reaction tubes in the shell-and-tube reactor can be the tube side of the reaction tube and the second side can be the shell side. As is appreciated in the art, various embodiments can have the first side of the reaction tubes as the shell side of the tubes and the second side of the reaction tubes can be the tube side. Additional examples of reactors in the various embodiments of the present disclosure include baffled tank and plug flow reactors. In various embodiments, the two or more reactors 101-1, 101-2 can be structurally identical reactors. Benefits of each of the two or more reactors 101-1, 101-2 being structurally identical include simplification of process calculations to determine, for example, promoter feed concentrations, reactor temperature control, rate of catalyst deactivation, and coolant duty requirements. In various embodiments, the reaction can be carried out in the liquid phase in a solvent. In such liquid phase embodiments the solvent can be put on the shell side of the reactor and the coolant can be on the tube side.

For the various embodiments, catalysts chosen for the two or more reactors can be similarly situated so that deactivation of the catalysts occurs at a substantially equivalent rate. Substantially equivalent rates include deactivation rates that are not necessarily equal but are within a range of one another such that the catalyst of the two or more reactors can economically be replaced at a common time. The catalyst of each reactor can be on a first side of the number of reaction tubes in each of the number of reactors. In various embodiments, the catalyst is on the tube side of the number of reaction tubes (e.g., where the first side of the number of reaction tubes is the tube side). Further embodiments of the present disclosure can include the catalyst on the shell side of the number of reaction tubes (e.g., where the first side of the number of reaction tubes is the shell side). For the various embodiments, a homogeneous or heterogeneous catalyst can be used. Examples of heterogeneous catalysts contain active components, such as nickel, manganese, molybdenum and/or vanadium containing complexes or salts, on a carrier, such as an alumina, silica, aluminosilicate, titania, magnesia and/or carbon. Examples of homogeneous oxidation catalysts include, but are not limited to, common complexes or salts.

For the various embodiments, the catalyst for the catalytic oxidation can be elements of groups Ib, IIb, IIIB, IVb, Vb, VIb, VIIb, IIIa, IVa, Va, VIa, VIII, and/or of the lanthanide group, such as Mo, Mn, Wo, Zn, Re, Au, Pd, Ag, V, Ru, La and/or Ti in different combinations and ratios, but also Sc, Y, Ce, Zr, Nb, Ta, Cr, Fe, Os, Co, Rh, Ir, Ni, Pd, Pt, Cu, Ga, In, Ge, Sn, Se, Te, As, Sb and/or Bi in different combinations and ratios with those mentioned herein. In various embodiments, the support for the catalyst include, but are not limited to, alumdum (a-alumina), glass wool, quartz, carborundum, and ion-exchange zeolites. The physical and chemical properties of the support can dictate the performance of the finished catalyst. Therefore, the support should be chosen according to the desired performance characteristics of the catalyst.

For the various embodiments, the process can be carried out in the absence or presence of a promoter. A promoter can enhance the activity and the selectivity of the catalyst, and improve the long-term stability of the catalyst. In the various embodiments of the present disclosure, a promoter can be one of aldehyde, like acetaldehyde, or an alkaline additive, like hydroxides of the group Ia and Ib, such as sodium hydroxide or magnesium hydroxide. In various examples, the promoter can be fed to the two or more reactors 101-1, 101-2 and can include chlorine-containing compounds and/or $NO_x$ (e.g., nitric oxides). When provided as a component of the catalyst itself, the total quantity of promoter metal(s) can be greater than 0.01 weight percent, based on the total weight of the catalyst. The total quantity of promoter metal(s) is generally less than 1 weight percent, based on the total weight of the catalyst. In various embodiments, gas-phase inhibitors can also be fed to suppress undesirable oxidation of the olefin (e.g., to carbon dioxide and water). Examples of such inhibitors include, but are not limited to, alkyl halides, aromatic hydrocarbons, amines, and organometallic compounds.

For the various embodiments, the two or more reactors 101-1, 101-2 each have an inlet 104, 106 that supplies a mixture comprising olefins and oxygen to the catalyst. The inlets 104, 106 can, in various embodiments, come from a common supply line 102.

For the various embodiments, olefins or mixtures thereof can be used. In various embodiments, olefin feedstock can be used that contains up to 50 weight percent of saturated compounds. In an embodiment of the present disclosure, the olefin is ethylene. Monoolefins and compounds containing two or more olefinic bonds, such as dienes, can be used. The olefins can be aliphatic or alicyclic. The olefin can be a simple hydrocarbon containing only carbon and hydrogen atoms; or alternatively, the olefin can be substituted at a carbon atom with an inert substituent. Example inert substituents include, but are not limited to, halides, ether, ester, alcohol, or aromatic moieties, preferably chloro, $C_{1-12}$-ether, ester, or alcohol moieties or $C_{6-12}$-aromatic moieties. Examples of olefins include, but are not limited to, propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including 1-octene, and other higher analogues olefins. Additional olefins of the present disclosure include, but are not limited to, butadiene, cyclopentadiene, dicyclopentadiene, styrene, ∞-methylstyrene, divinylbenzene, allyl chloride, allyl alcohol, allyl ether, allyl ethyl ether, allyl butyrate, allyl acetate, allyl benzene, allyl phenyl ether, allyl propyl ether, and allyl anisole. The olefin can be an unsubstituted or substituted $C_{2-12}$-olefin, more preferably, an unsubstituted or substituted-$C_{2-10}$-olefin.

For the various embodiments, a single coolant drum 105 supplies coolant fluid at a common temperature to coolant fluid inlet streams 118, 120 of each of the two or more reactors 101-1, 101-2. FIG. 1 illustrates only one coolant fluid inlet stream per reactor. Further embodiments, however, can include more than one coolant fluid inlet stream per reactor. The coolant fluid passes through each of the two or more reactors 101-1, 101-2 and removes heat generated by the oxidation reaction from the number of reaction tubes 109-1A, 109-1B, 109-1N and 109-2A, 109-2B, 109-2N. The coolant fluid flows into the single coolant drum 105 from coolant fluid outlet streams 114, 116 of each of the two or more reactors 101-1, 101-2. FIG. 1 illustrates only one coolant fluid outlet stream per reactor. Further embodiments, however, can include more than one coolant fluid outlet stream per reactor. In various embodiments the coolant fluid is an aqueous solution. In various embodiments, the single coolant drum 105 can be a steam drum as is known in the art. The single coolant drum is the cooling system for the two or more reactors of the olefin oxidation system. Olefin oxidation systems that use multiple reactors that are known in the art use multiple coolant drums. In the present disclosure there is one single coolant drum for the two or more reactors that must handle the cooling of the two or more reactors. Consequently, the cooling duty of the single coolant drum of the present disclosure is increased compared to the cooling duty of an individual coolant drum of systems with multiple coolant drums for multiple reactors. So, embodiments of the present disclosure can reduce pressure (e.g., stress load) on the inlets to the single coolant drum and distribute the load (e.g., stress load) on the single coolant drum more evenly by having the inlets flow into opposing ends of the single coolant drum.

Figure 2:
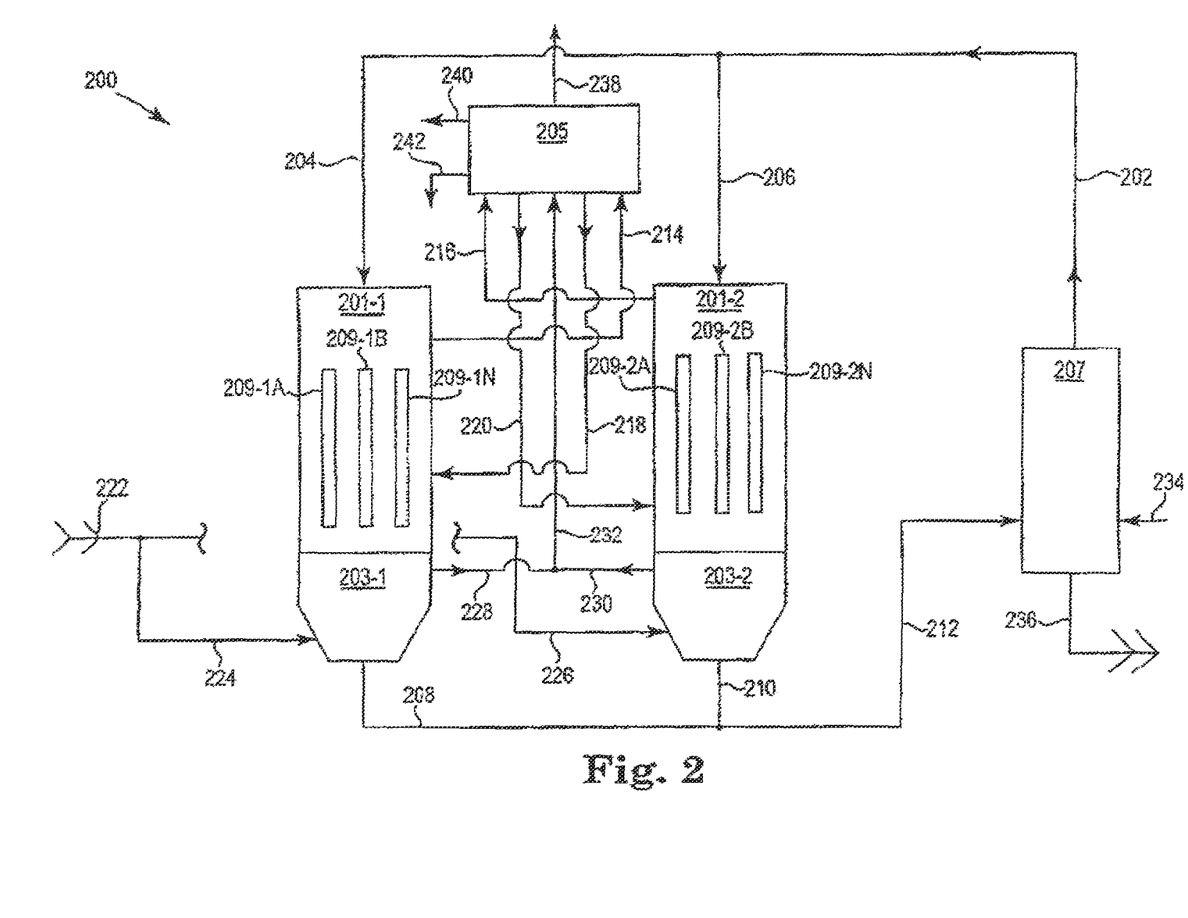
FIG. 2 provides a schematic of a process for producing an oxidized olefin product according to an embodiment of the present disclosure.

Referring to FIG. 2, there is illustrated a schematic of a system 200 for the production of an oxidized olefin product. For the system 200, two or more reactors 201-1, 201-2 include a number of reaction tubes 209-1A, 209-1B, 209-1N and 209-2A, 209-2B, 209-2N, where N represent N number of reaction tubes, containing a catalyst for catalytic oxidation of olefins.

For the various embodiments, the two or more reactors 201-1, 201-2 each have an inlet 204, 206 that supplies a mixture comprising olefins and oxygen to the catalyst. The inlets 204, 206 can, in various embodiments, come from a common supply line 202. The common supply line 202, in various embodiments, can be preheated via a cross heat exchanger 207. According to the present disclosure, the cross heat exchanger 207 can be used to remove heat from a common oxidized olefin product stream 212, which is composed of oxidized olefin product outlets 208, 210 for each of the two or more reactors 201-1, 201-2. The oxidized olefin product outlets of the two or more reactors can contain unreacted components of the inlet streams. The heat removed from the common oxidized olefin product stream 212 can be used to preheat a common supply line 234 including a mixture comprising olefins and oxygen to become common supply line 202. Stream 236 contains the cooled oxidized olefin product of the two or more reactors and can be sent to be further processed as is known in the art.

For the various embodiments, a single coolant drum 205 supplies coolant fluid at a common temperature to coolant fluid inlet streams 218, 220 of each of the two or more reactors 201-1, 201-2. FIG. 2 illustrates only one coolant fluid inlet stream per reactor. Further embodiments, however, can include more than one coolant fluid inlet stream per reactor. The coolant fluid passes through each of the two or more reactors 201-1, 201-2 and removes heat from the number of reaction tubes 209-1A, 209-1B, 209-1N and 209-2A, 209-2B, 209-2N. The coolant fluid flows into the single coolant drum 205 from coolant fluid outlet streams 214, 216 of each of the two or more reactors 201-1, 201-2. FIG. 2 illustrates only one coolant fluid outlet stream per reactor. Further embodiments, however, can include more than one coolant fluid outlet stream per reactor. Coolant drums in embodiments of the present disclosure can have an outlet stream to a steam header 238, a continuous/intermittent blowdown outlet 240, and, as is common in the art, a condensate from start up outlet 242.

For the various embodiments, the coolant fluid outlet streams 214, 216 of each of the two or more reactors 201-1, 201-2 flow into the single coolant drum 205 through inlets on opposing ends of the single coolant drum 205. In the various embodiments, the coolant fluid outlet steams 214, 216 and coolant inlet streams 218, 220 of each of the two or more reactors 201-1, 201-2 cross over one another to provide stress relief for fluid flow and load forces on vessel nozzles at the single coolant drum 205. By reducing piping stress and load forces on vessel nozzles there is a corresponding reduction in the opportunity for leaks and/or emissions, as well as a reduction in the possibility of piping material fatigue, further reducing downtime and increasing production.

For the various embodiments, the coolant fluid outlet streams 214, 216 and coolant inlet streams 218, 220 of each of the two or more reactors 201-1, 201-2 is such that substantially equivalent cooling is provided for each of the two or more reactors 201-1, 201-2. Substantially equivalent cooling includes cooling loads that are not necessarily equal but are within a range of one another such that the temperatures of the two or more reactors can be maintained at a common temperature. For the embodiments of the present disclosure, the reactor coolant fluid piping can be designed for systems with two or more structurally identical reactors, systems with two or more different reactors, and combinations thereof.

For the various embodiments, the single coolant drum 205 provides enough coolant capacity to maintain a common temperature across the catalyst contained in the number of reaction tubes 209-1A, 209-1B, 209-1N and 209-2A, 209-2B, 209-2N of each of the two or more reactors 201-1, 201-2. According to the present disclosure, a common temperature across the catalyst of each reactor allows for more uniform deactivation of the catalyst and can help to decrease the opportunity for runaway reactions.

For the various embodiments, the catalyst contained in the number of reaction tubes 209-1A, 209-1B, 209-1N and 209-2A, 209-2B, 209-2N of each of the two or more reactors 201-1, 201-2 deactivates at a substantially equivalent rate. Since the catalyst in the two or more reactors deactivates at a substantially equivalent rate the point at which the catalysts of the two or more reactors will need to be replaced due to a number of economic factors (e.g., improvement in performance with fresh catalyst charge vs. the cost of a fresh catalyst charge) can be at a common time. According to the present disclosure, the downtime from having to replace deactivated catalyst of the multiple reactors will be decreased and consequently the overall system efficiency can increase.

In various embodiments, a promoter concentration feed of each of the two or more reactors 201-1, 201-2 can be maintained within a tolerance level. According to the present disclosure the promoter concentration feed can be maintained at a concentration such that the overall yield of desired oxidized olefin product can be increased.

For the various embodiments, aftercoolers 203-1, 203-2 can be connected to each of the two or more reactors 201-1, 201-2 to preheat a coolant makeup supply. In various embodiments, the coolant makeup supply can be a boiler feed water (BFW) supply. According to the present disclosure the coolant makeup supply comes from a common coolant makeup supply line 222. The common coolant makeup supply line 222 can split into coolant makeup supply inlets 224, 226 for the aftercoolers 203-1, 203-2. As is illustrated in FIG. 2, preheated coolant makeup outlets 228, 230 of each aftercooler 203-1, 203-2 can join to form a preheated coolant makeup outlet 232 that is fed to the single coolant drum 205.

In various embodiments the preheated coolant makeup outlets 228, 230 of each aftercooler 203-1, 203-2 can be fed to an overall aftercooler specific coolant drum. Such embodiments can lessen the overall coolant duty required of the single coolant drum 205. According to the present disclosure, each preheated coolant makeup outlet 228, 230 of each aftercooler 203-1, 203-2 can be fed to an aftercooler specific coolant drum for each aftercooler. Embodiments of the present disclosure also contemplate multiple aftercooler specific coolant drums for each aftercooler with a single cross heat exchanger for the oxidized olefin product outlets of each of the two or more reactors.

For the various embodiments of the present disclosure, the reaction can be carried out in the liquid phase in a solvent. As used herein, weight percentages of olefin used in the reaction take into consideration the use of a solvent. However, in various embodiments of the present disclosure a solvent is not required. Solvents that can be used in a liquid phase system and method for producing an olefin oxide are known in the art, for example, hydrocarbons, aromatic hydrocarbons, ketones or esters, such as fully esterified polyacyl esters. Examples of solvents include, but are not limited to, halogenated benzenes, monohalogenated benzenes, dihalogenated benzenes. Further examples of solvents in the various embodiments include, but are not limited to, monobromobenzene, chlorobenzene, o- or m-dicholorbenzne o-, m- or p-dibromobenzene, o-, m- or p-bromochlorobenzene, o-, m- or p-dichlorobenzene. Other suitable solvents are polyethers, polyesters, polyalcohols or halogenated, preferably chlorinated, aliphatic alcohols, such as 2-chloro-1-propanol, 3-chloro-1-propanol, 1-bromo-2-propanol, dichloro- or dibromo-propanols.

For the various embodiments, a method of producing oxidized olefins can include supplying a mixture comprising olefins and oxygen to two or more reactors from a common supply line. The common supply line can contain an olefin as discussed herein. The quantity of olefin in the method can vary over a wide range, provided that the corresponding oxidized olefin is produced. The quantity of olefin depends upon the specific process features, which include, for example, the design of the reactor, the specific olefin, and economic and safety considerations. Those skilled in the art will appreciate how to determine a suitable range of olefin concentrations for the specific process features. For example, on a molar basis an excess of olefin can be used relative to the oxygen. This excess of olefin enhances the selectivity to olefin oxide and reduces the selectivity to combustion products (e.g., carbon dioxide). The quantity of the olefin can be greater than 1 mole percent, based on the total moles of olefin, oxygen, and solvent. The quantity of the olefin can be less than 99 mole percent, based on the total moles of olefin, oxygen, and solvent.

For the various embodiments, the olefin is contacted with oxygen, such as essentially pure molecular oxygen, or an oxygen-containing gas, such as air or oxygen diluted with nitrogen or carbon dioxide. In embodiments where the olefin is contacted with an oxygen-containing gas, the oxygen concentration in the gas can be from 15 to 60 volume percent. In various embodiments, other sources of oxygen can include ozone and nitrogen oxides, such as nitrous oxide. Air, molecular oxygen or oxygen diluted with carbon dioxide can also be used. The quantity of oxygen in the common supply line can vary over a wide range provided that the quantity is sufficient for producing the desired olefin oxide. Considerations in the quantity of oxygen in the common supply line include, but are not limited to, safety considerations (e.g., avoiding flammable compositions at higher quantities of oxygen). In the various embodiments, the number of moles of oxygen per mole of olefin is less than 1. For example, the quantity of oxygen can be between 0.01 mole percent and 10 mole percent, based on the total moles of olefin, oxygen and solvent.

For the various embodiments, the mixture is reacted in each of the two or more reactors to produce a product stream comprising the oxidized olefins. In the various embodiments, the method of the present disclosure can be conducted at a temperature of from 100° C. to 300° C. In the various embodiments, the pressure of the multiple reactors can range from 0.1 to 10 MPa. The residence time in each of the two or more reactors is generally 0.5 seconds to 1800 seconds (30 minutes).

For the various embodiments, the product stream from each of the two or more reactors is joined into a single common product stream of the oxidized olefins. In the various embodiments of the present disclosure, the single common product stream can enter a cross heat exchanger to remove heat from the product with the common mixture supply of olefins and oxygen.

For the various embodiments, coolant fluid is supplied at a common temperature from a single coolant drum to the two or more reactors via a coolant fluid inlet stream of each of the two or more reactors. The coolant fluid from each of the two or more reactors is supplied to the single coolant drum by a coolant fluid outlet stream of each of the two or more reactors. In various embodiments of the present disclosure, the single coolant drum can be connected to an aftercooler of each of the two or more reactors via a preheated coolant makeup outlet of each aftercooler. Embodiments of the present disclosure also contemplate an aftercooler specific coolant drum connected to the preheated coolant makeup outlet of each aftercooler of the two or more reactors.

EXAMPLES

The following examples further illustrate the present disclosure in detail, but are not to be construed to limit the scope of the disclosure. The below prophetic examples illustrate temperature or pressure measurements of a system for producing an oxidized olefin according to, but not limited to, a system such as FIG. 2.

Each of the below examples, and corresponding figures, plot idealized measurements against a unity line. The unity line represents "perfect control" of the temperature and/or pressure of the system. As can be appreciated by one in the art, such a situation is not possible in the real world. As such, the examples section indicates temperature and/or pressure readings that are expected in an ideal system described in the present disclosure to further draw distinction between the present disclosure and prior solutions.

Example 1

FIG. 3

Figure 3:
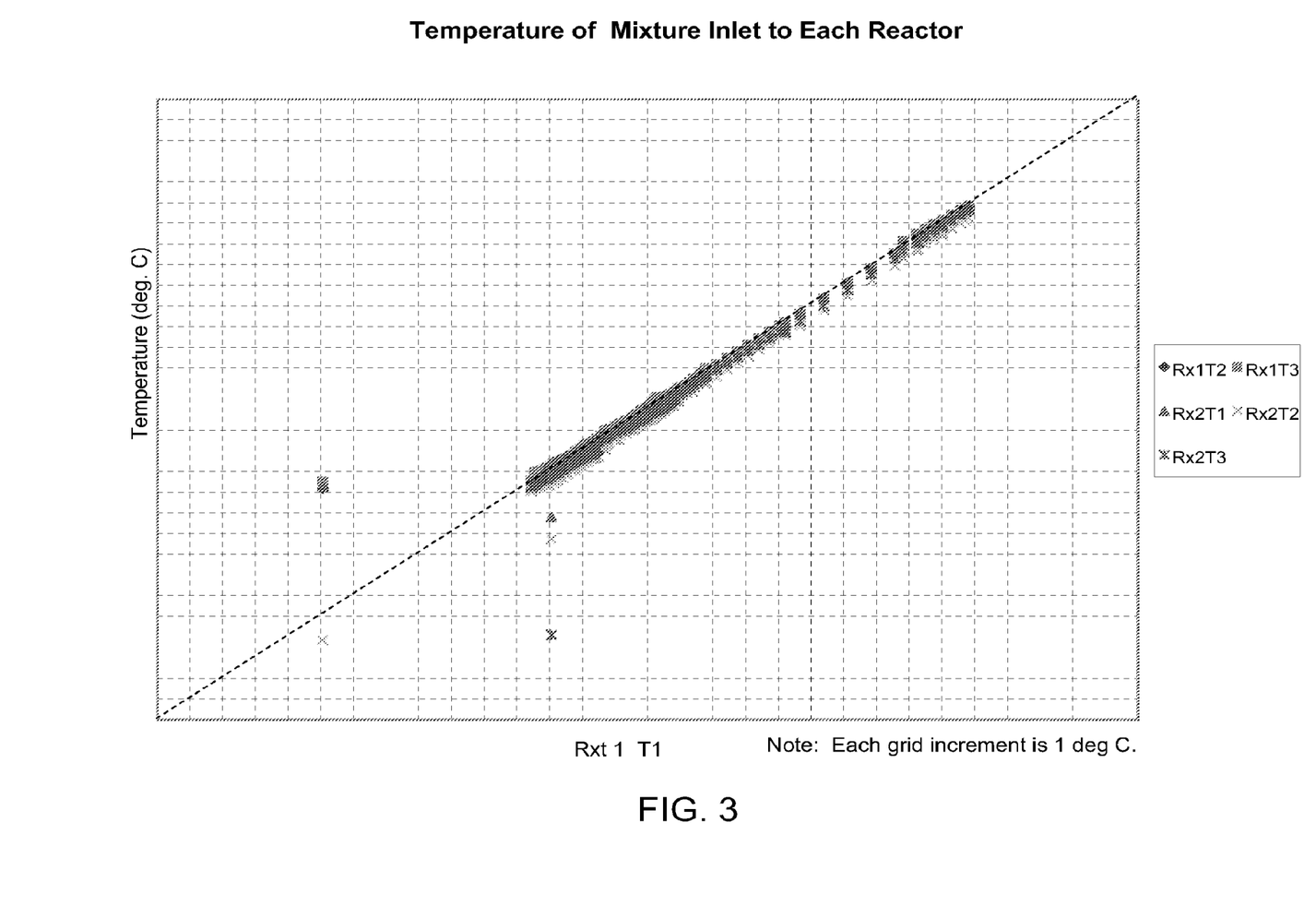
FIG. 3 provides a plot of temperatures of a mixture inlet to each reactor according to an embodiment of the present disclosure.

FIG. 3 is a representative plot of a temperature of the mixture, comprising olefins and oxygen, supplied to the two reactors, Rx 1 and Rx 2 (e.g., FIG. 2, stream 204 to reactor 201-1 and stream 206 to reactor 201-2). Temperature readings of the same value are represented by the points overlapping each other. Such an ideal situation is represented by the dotted line with a slope of 1, also called the unity line. As is illustrated by FIG. 3, the temperature readings of the mixture, comprising olefins and oxygen, at the inlet of each reactor are predicted to be essentially the same (e.g., the temperature readings follow the unity line closely). The essentially same temperature readings of the inlet of each reactor are a direct result of the greater controllability of one coolant drum and the single cross heat exchanger for the two reactors, as discussed herein.

Example 2

FIG. 4

Figure 4:
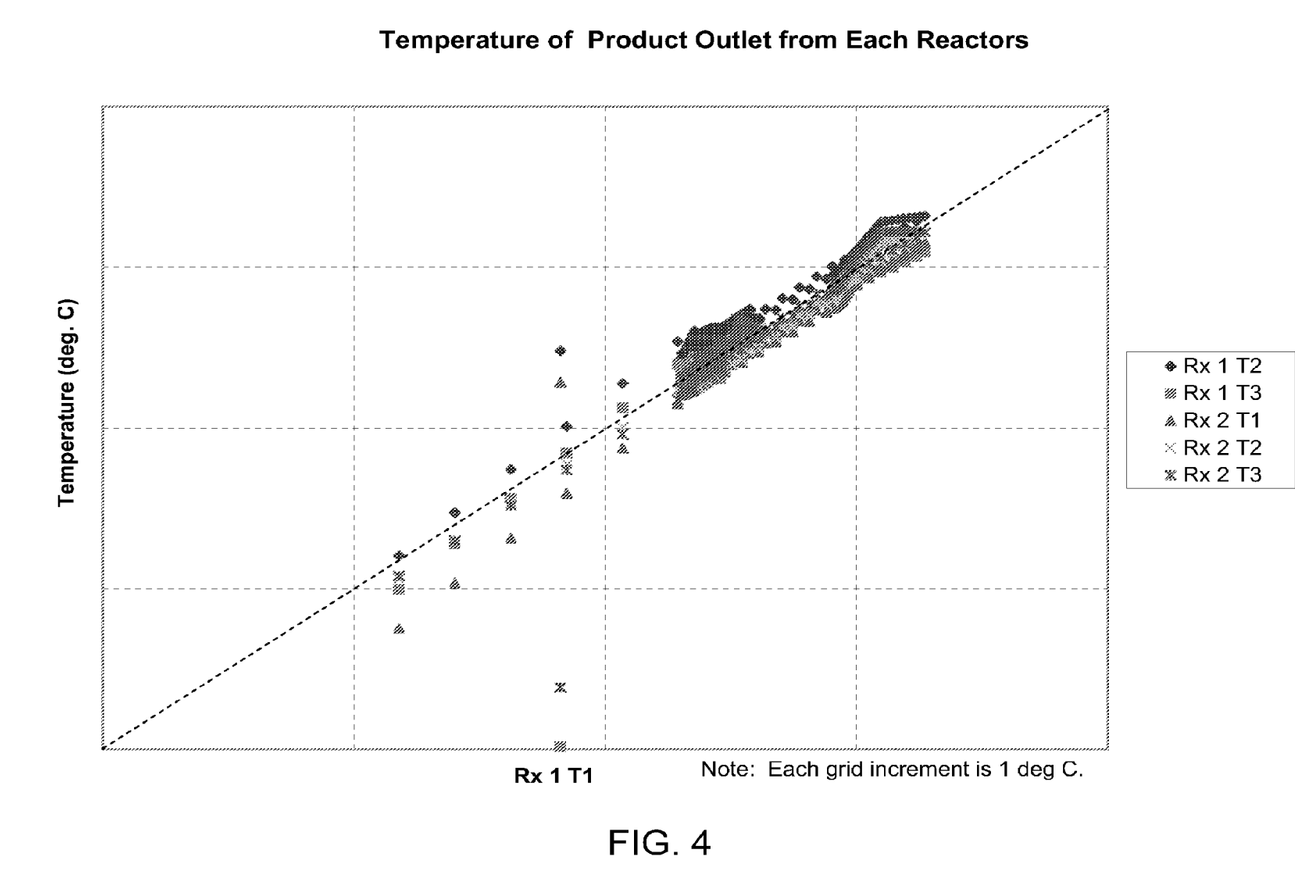
FIG. 4 provides a plot of temperatures of a product outlet from each reactor according to an embodiment of the present disclosure.

FIG. 4 is a representative plot of a temperature of the product outlet, comprising oxidized olefins, of the two reactors Rx 1 and Rx 2 (e.g., FIG. 2, stream 208 from reactor 201-1 and stream 210 from reactor 201-2). As is illustrated by FIG. 4, the temperature measurements of the product outlet stream of each reactor, Rx 1 and Rx 2, are predicted to be essentially the same. Accordingly, the temperature measurements are similar to the unity line. The essentially same temperature readings of the product outlet stream of each reactor are a direct result of the greater controllability of one coolant drum and the single cross heat exchanger for the two reactors, as discussed herein.

Example 3

FIG. 5

Figure 5:
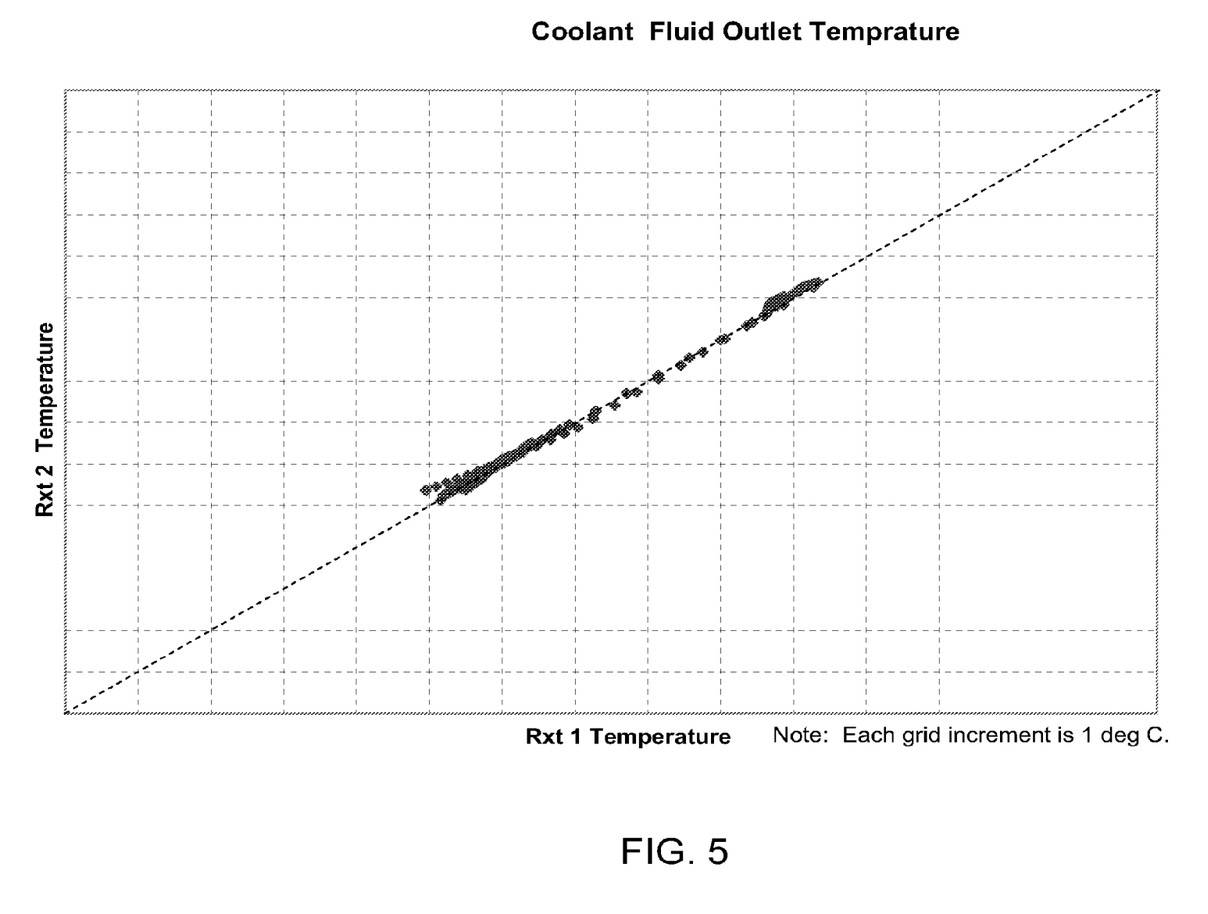
FIG. 5 provides a plot of coolant fluid outlet temperature according to an embodiment of the present disclosure.

FIG. 5 is a representative plot of the temperature of a coolant fluid outlet of each of the reactors Rx 1 and Rx 2 (e.g., FIG. 2, stream 214 from reactor 201-1 and stream 216 from reactor 201-2). Temperature indications of the same value for each reactor would result in a line of a slope of 1, also known as the unity line indicated by the dashed line on FIG. 5. As is illustrated by FIG. 5, the temperature measurements of the coolant fluid outlet stream of each reactor are predicted to be substantially equivalent. The precise nature of the coolant fluid outlet stream temperature from the two reactors is predicted to represent improved coolant temperature control, as compared to previous approaches (e.g., FIG. 6).

Comparative Example A

FIG. 6

Figure 6:
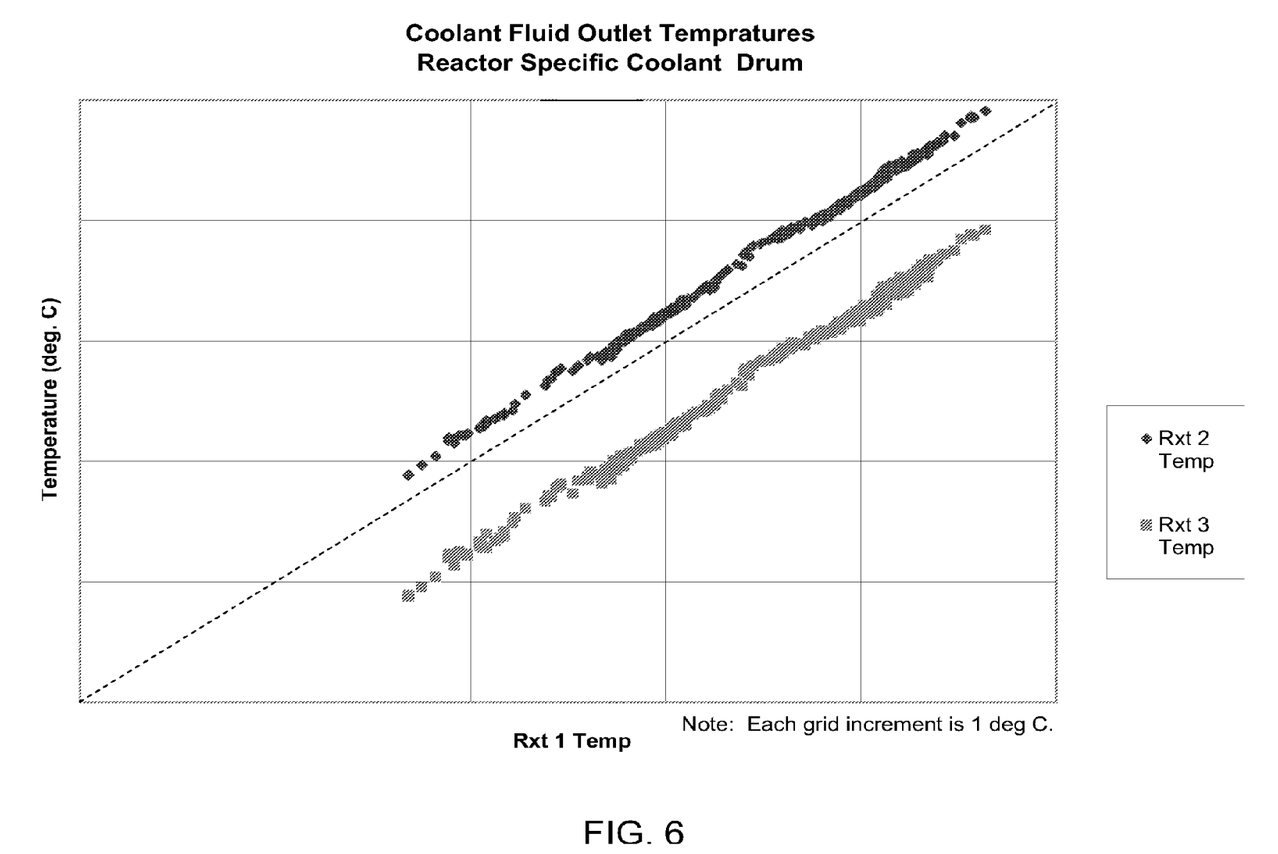
FIG. 6 provides a plot of coolant fluid outlet temperatures of a system with multiple reactor specific coolant drums.

FIG. 6 is a representative plot of a system for producing oxidized olefins in which three (3) reactors each have a reactor specific coolant drum. FIG. 6 plots coolant fluid outlet temperatures of each reactor, where the temperature for Rx 1 is plotted along the x-axis and the temperature for reactors Rx 2 and Rx 3 are plotted on the y-axis. Temperature reading of the same value for each reactor would result in a line of a slope of 1, also known as the unity line indicated by the dashed line on FIG. 6. This dashed line is the equal temperature line, where if all three reactors Rx 1, Rx 2 and Rx 3 shared a common steam drum, as discussed herein, the temperatures for all three reactors is predicted to fall directly on this dashed line.

As is illustrated in FIG. 6, the temperatures of each coolant outlet of Rx 1, Rx 2 and Rx 3 are predicted to be different, as neither Rx 2 nor Rx 3 coolant outlet temperatures are predicted to fall on the unity line. Among the potential reasons for this variation may be variable catalyst performance in addition to the lack of a single steam drum. As compared to the present disclosure (e.g., FIG. 5), FIG. 6, which illustrates a system for producing oxidized olefins where each reactor has a reactor specific coolant drum, shows greater variation (e.g., imprecision) in coolant outlet temperature.

Example 4

FIG. 7

Figure 7:
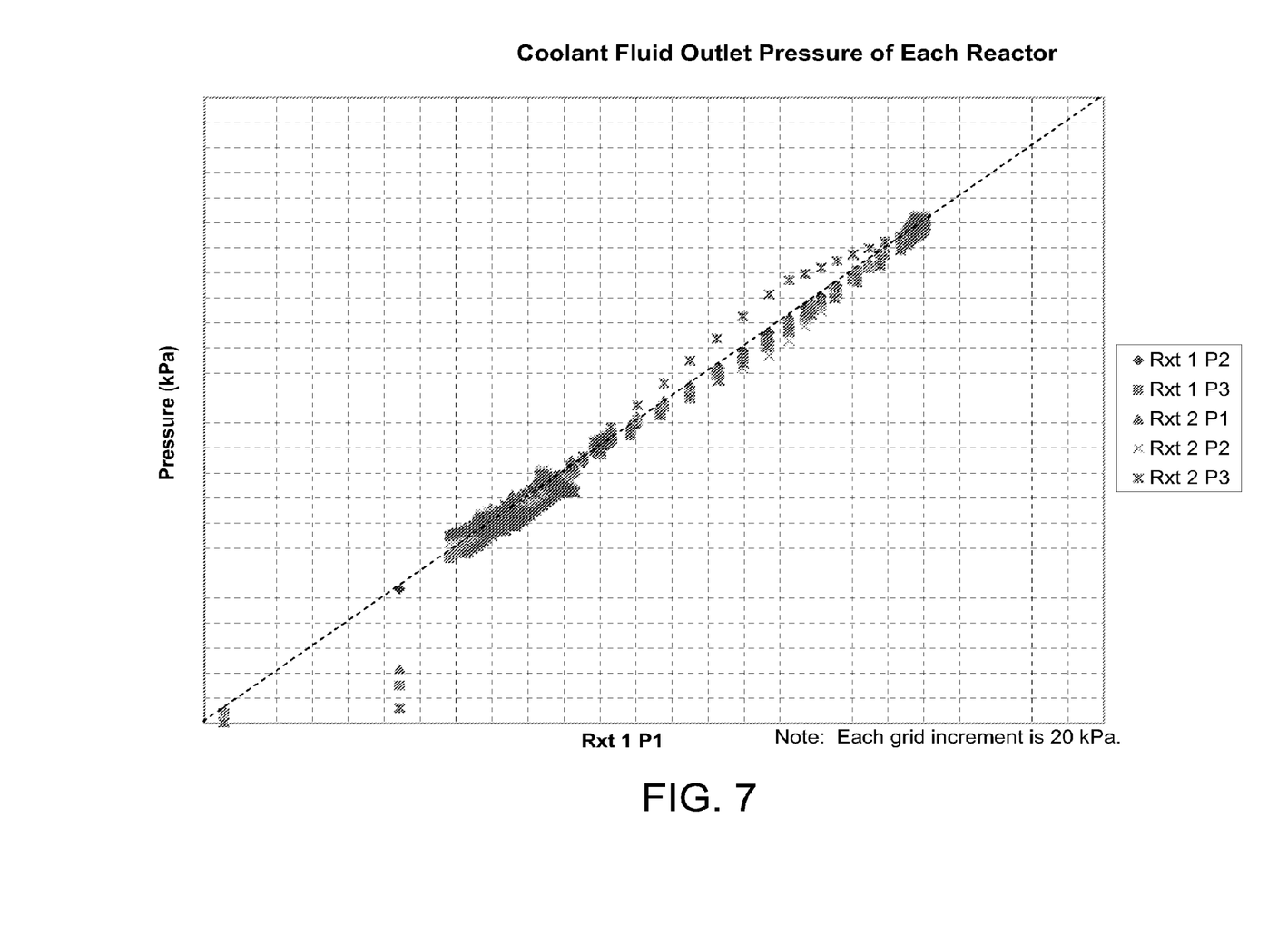
FIG. 7 provides a plot of coolant fluid outlet pressure according to an embodiment of the present disclosure.

FIG. 7 is a representative plot of the pressure of a coolant fluid outlet of each of the reactors Rx 1 and Rx 2 (e.g., FIG. 2, stream 214 from reactor 201-1 and stream 216 from reactor 201-2). Pressure readings of the same value for each reactor would result in a line of a slope of 1, also known as the unity line indicated by the dashed line on FIG. 7. As is illustrated by FIG. 7, the pressure readings of the coolant fluid outlet stream of each reactor are predicted to be substantially equivalent as they fall closely on the unity line.

What is claimed:

1. A system for producing oxidized olefins, comprising:
   two or more reactors, each of the two or more reactors including a number of reaction tubes each including a first surface defining a first side and a second surface opposite the first surface that defines a second side of each of the number of reaction tubes;
   a catalyst for catalytic oxidation of olefins on the first side of the number of reaction tubes;
   an inlet to each of the two or more reactors that supplies a mixture comprising olefins and oxygen to the catalyst;
   a common supply line for supplying the mixture comprising olefins and oxygen to each inlet of the two or more reactors;
   a product outlet from each of the two or more reactors for receiving a product stream comprising the oxidized olefins; and
   only one steam drum connected to the two or more reactors, where coolant fluid passing through the two or more reactors produces a vapor phase to remove heat from the number of reaction tubes by a phase change of the coolant fluid, where the vapor phase flows into the only one steam drum from a number of coolant fluid outlet streams of each of the two or more reactors and the only one steam drum separates the vapor phase from a liquid phase of the coolant fluid, where the liquid phase of the coolant fluid is supplied at a common temperature to a number of coolant fluid inlet streams of each of the two or more reactors.

2. The system of claim 1, wherein the system comprises a single cross heat exchanger that removes heat from a number of components in the single common product stream.

3. The system of claim 1, where the number of coolant fluid outlet streams of each of the two or more reactors flow into the only one steam drum through inlets on opposing ends of the only one steam drum.

4. The system of claim 1, where pipes for the coolant fluid outlet and inlet streams to and from each of the two or more reactors cross over one another to provide stress relief for fluid flow and load forces on the only one steam drum.

5. The system of claim 1, where an aftercooler is connected to each of the two or more reactors to preheat a coolant makeup supply.

6. The system of claim 1, where the catalyst contained in the number of reaction tubes of each of the two or more reactors deactivates at a substantially equivalent rate.

7. The system of claim 1, where a common coolant fluid temperature is maintained across the catalyst contained in the number of reaction tubes of each of the number of reactors.

8. The system of claim 1, where the coolant fluid outlet and inlet streams provide substantially equivalent cooling of each of the two or more reactors.

9. A method for producing oxidized olefins, comprising:
supplying a mixture comprising olefins and oxygen to two or more reactors from a common supply line;
reacting the mixture in each of the two or more reactors to produce a product stream comprising the oxidized olefins;
joining the product stream from each of the two or more reactors into a single common product stream comprising the oxidized olefins;
supplying a coolant fluid from each of the two or more reactors to only one steam drum by a number of coolant fluid outlet streams of each of the two or more reactors; and
supplying the coolant fluid at a common temperature from the only one steam drum to each of the two or more reactors to remove heat produced in the two or more reactors during the reaction of the mixture.

10. The method of claim 9 further comprising removing heat from a number of components in the single common product stream with a single cross heat exchanger.

11. The method of claim 9, where the two or more reactors include a number of reaction tubes including a first side and a second side and a catalyst for catalytic oxidation of olefins on the first side of the number of reaction tubes and reacting the mixture occurs at a rate such that the catalyst in the number of reaction tubes of each of the number of reactors deactivates at a common rate.

12. The method of claim 11, where the method includes maintaining a common coolant fluid temperature across the catalyst contained in the number of reaction tubes of each of the number of reactors.

13. The method of claim 9, where the method includes maintaining a promoter concentration feed of each of the two or more reactors within a tolerance level.

14. The method of claim 9, where the method includes: preheating a coolant makeup supply with an aftercooler connected to each of the two or more reactors; and feeding a preheated coolant makeup outlet of each aftercooler to the only one steam drum.

* * * * *